US012643848B2

(12) United States Patent
Chen et al.

(10) Patent No.: US 12,643,848 B2
(45) Date of Patent: Jun. 2, 2026

(54) SEPARATION AND PURIFICATION METHOD OF 2-NITROETHANOL

(71) Applicant: Fudan University, Shanghai (CN)

(72) Inventors: Fener Chen, Shanghai (CN); Minjie Liu, Shanghai (CN)

(73) Assignee: Fudan University, Shanghai (CN)

( * ) Notice: Subject to any disclaimer, the term of this patent is extended or adjusted under 35 U.S.C. 154(b) by 500 days.

(21) Appl. No.: 18/361,533

(22) Filed: Jul. 28, 2023

(65) Prior Publication Data

US 2024/0018088 A1 Jan. 18, 2024

(30) Foreign Application Priority Data

Mar. 21, 2023 (CN) ......................... 202310278933.6

(51) Int. Cl.
*C07C 201/16* (2006.01)

(52) U.S. Cl.
CPC .................................. *C07C 201/16* (2013.01)

(58) Field of Classification Search
CPC .... C07C 201/16; C07C 201/12; C07C 205/15
See application file for complete search history.

(56) References Cited

PUBLICATIONS

Wayland E. Noland, "2-nitroethanol", Organic Syntheses, 1961, vol. 41, p. 67.

Karol Grela et al., "A convenient synthesis of deuterium labeled tertiary aliphatic nitro ketones and nitriles—starting materials for preparation of deuterated cyclic nitrones, isomeric hydroxylamines, and corresponding C-nitroso compounds." Tetrahedron, 2010, vol. 66, No. 20, pp. 3614-3622.

Jagat C. Borah et al., "LaCI3•7H2O-Promoted Regioselective Ring Opening of Epoxides Using NaNO2 in Ether-Water System: A Facile Synthesis of 2-Nitroalcohols", Synthetic Communications, 2005, vol. 35, No. 6, pp. 873-878.

Wayland E. Noland et al., "The Nitroethylation of Indole. A New Synthesis of Tryptamine", Journal of the American Chemical Society, 1954, vol. 76 ,No. 12, pp. 3227-3228.

*Primary Examiner* — Jafar F Parsa

(57) ABSTRACT

A separation and purification method of 2-nitroethanol, including: (a) reacting paraformaldehyde with nitromethane in the presence of a base to obtain a mixture of 2-nitroethanol (I), 2-nitro-1,3-propanediol (II) and tris(hydroxymethyl) nitromethane (III); and (b) selecting an extraction solvent in which 2-nitroethanol (I), 2-nitro-1,3-propanediol (II) and tris(hydroxymethyl) nitromethane (III) are different in solubility; adding the extraction solvent to the mixture followed by extraction, separation, and vacuum concentration to obtain the 2-nitroethanol (I).

6 Claims, No Drawings

SEPARATION AND PURIFICATION METHOD OF 2-NITROETHANOL

CROSS-REFERENCE TO RELATED APPLICATIONS

This application claims the benefit of priority from Chinese Patent Application No. 202310278933.6, filed on Mar. 21, 2023. The content of the aforementioned application, including any intervening amendments thereto, is incorporated herein by reference in its entirety.

TECHNICAL FIELD

This application relates to organic chemistry, and more specifically to a separation and purification method of 2-nitroethanol.

BACKGROUND

2-Nitroethanol (I) is an important raw material for the preparation of amide alcohol antibiotics, and has great potential in medicine and veterinary drug.

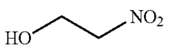

(I)

Wayland E. Noland, et al. (*Org. Synth.,* 1961, 41, 67) disclosed a method for preparing the compound (I) from paraformaldehyde and nitromethane under the catalysis of potassium hydroxide, in which diphenyl ether was added, and 2-nitroethanol was collected by high-temperature azeotropic distillation. Unfortunately, this method has a great risk of explosion, as well as poor yield (only 4649% yield). Grela et al. (K. Grela, L. Konopski. A convenient synthesis of deuterium labeled tertiary aliphatic nitro ketones and nitriles—starting materials for preparation of deuterated cyclic nitrones, isomeric hydroxylamines, and corresponding C-nitroso compounds. Tetrahedron, 2010, 66(20):3614-3622) disclosed another method for preparing 2-nitroethanol from paraformaldehyde and nitromethane under the catalysis potassium hydroxide. This method requires extremely excessive consumption of nitromethane to improve the reaction selectivity and is thus not suitable for industrial production. Borah et al. (J. C. Borah, S. Gogoi, J. Boruwa, N. C. Barua. $LaCl_3 \cdot 7H_2O$-Promoted Regioselective Ring Opening of Epoxides Using $NaNO_2$ in Ether-Water System: A Facile Synthesis of 2-Nitroalcohols, Synthetic Communications, 2005, 35(6), 873-878. DOI: 10.1081/SCC-200051043) disclosed a method for preparing 2-nitroethanol from ethylene oxide and sodium nitrite under the action of lanthanum chloride. This method requires excess sodium nitrite and heavy metal salts, causing environmental pollution. Noland et al. (Wayland E. Noland and Philip J. Hartman. The Nitroethylation of Indole. A New Synthesis of Tryptamine, *Journal of the American Chemical Society,* 1954, 76 (12), 3227-3228) disclosed a method for preparing 2-nitroethanol by reacting 2-iodoethanol with silver nitrite. This method requires expensive reagents, and is not suitable for large-scale production.

SUMMARY

In view of the deficiencies in the prior art, this application provides a preparation method of 2-nitroethanol, which has excellent safety, low cost and high yield.

This application provides a separation and purification method of 2-nitroethanol (I), including:

(a) reacting paraformaldehyde with nitromethane under the catalysis of a base to obtain a mixture of 2-nitroethanol (I), 2-nitro-1,3-propanediol (II) and tris(hydroxymethyl) nitromethane (III), as shown in the following reaction scheme:

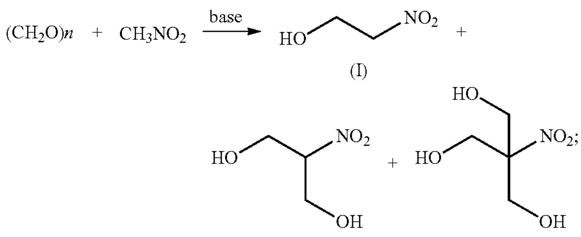

(I) (II) (III)

and (b) selecting an extraction solvent in which the 2-nitroethanol (I), 2-nitro-1,3-propanediol (II) and tris(hydroxymethyl) nitromethane (III) are different in solubility; adding the extraction solvent to the mixture followed by extraction, separation, and vacuum concentration to obtain the 2-nitroethanol (I);

wherein the extraction solvent is one or more of $C_3$~$C_9$ aliphatic esters;

a mass ratio of the extraction solvent to the paraformaldehyde is (1~10): 1;

the extraction is performed at −20~60° C. in a kettle equipment or a continuous extraction equipment; and the vacuum concentration is performed under a vacuum degree of 0.1~10 mmHg at 0~60° C.

In an embodiment, after the reaction is completed, the reaction mixture is adjusted to 2-4 with acid and concentrated to recover excess nitromethane. Then the reaction mixture was added with the extraction solvent for extraction and separation, and the extraction solvent is collected and dried under reduced pressure to recover to obtain light-yellow oily 2-nitroethanol.

In an embodiment, the extraction solvent is selected from the group consisting of butyl propionate, amyl propionate, propyl butyrate, butyl butyrate, isobutyl butyrate, tert-butyl butyrate, amyl butyrate, propyl isobutyrate, butyl isobutyrate, propyl valerate, isopropyl valerate, butyl valerate, isobutyl valerate, tert-butyl valerate, ethyl cyclopentanecarboxylate, propyl cyclopentanecarboxylate, and a mixture thereof.

In an embodiment, the extraction solvent is selected from the group consisting of propyl butyrate, butyl butyrate, isobutyl butyrate, propyl isobutyrate, butyl isobutyrate, propyl valerate, isopropyl valerate, and a mixture thereof, which are cheap, have good extraction effects, and are convenient for recovery.

In an embodiment, the mass ratio of the extraction solvent to the paraformaldehyde is (1~5): 1. 2-nitroethanol (I) can be successfully extracted.

In an embodiment, the extraction is performed at −20~30° C., at which the pure 2-nitroethanol (I) can be effectively extracted and separated.

In an embodiment, the continuous extraction equipment is a continuous membrane extraction-membrane separation equipment, a continuous micromixer mixing-microchannel reactor extraction-gravity sedimentation separation equipment, and a continuous centrifugal mixing-centrifugal separation equipment.

In an embodiment, the vacuum concentration is performed under a vacuum degree of 0.1~5 mmHg at 0~40° C.

Compared with the prior art, this application has the following beneficial effects.

Regarding the method provided in this application, purified 2-nitroethanol product is obtained from a crude product through extraction with a specific solvent and separation. Compared with the existing synthesis methods or post-treatment purification methods, the method provided herein has low risk of explosion, readily-available extraction solvent, mild extraction and separation conditions, excellent safety, simple operation, and high purity and yield (80%-85%), and has a promising industrial application prospect.

DETAILED DESCRIPTION OF EMBODIMENTS

This application will be described in detail below with reference to the embodiments, but these embodiments are not intended to limit the scope of this application.

Example 1

1.5 kg of Paraformaldehyde and 10 kg of nitromethane were added in a dry batch reactor, stirred, and then slowly added dropwise with 0.05 kg of a solution of sodium hydroxide in methanol. The reaction mixture was reacted under reflux for 0.5 h, cooled to room temperature, adjusted to pH 2-4 with concentrated sulfuric acid, and concentrated under vacuum to recover nitromethane. Then the reaction mixture was added with 3 kg of propyl butyrate at 20~25° C. for extraction, and the propyl butyrate layer was collected, and dried under vacuum to recover the propyl butyrate (vacuum degree: 1 mmHg, and temperature: 20~25° C.), so as to obtain 3.73 kg of light-yellow oily 2-nitroethanol (82% yield, 98% purity (GC)).

Example 2

1.5 kg of Paraformaldehyde and 10 kg of nitromethane were added in a dry batch reactor, stirred, and then slowly added dropwise with 0.05 kg of a solution of sodium hydroxide in methanol. The reaction mixture was reacted under reflux for 0.5 h, cooled to room temperature, adjusted to pH 2~4 with concentrated hydrochloric acid, and concentrated under vacuum to recover nitromethane. Then the reaction mixture was added with 3 kg of butyl butyrate at 25~30° C. for extraction, and the butyl butyrate layer was collected, and dried under vacuum to recover the butyl butyrate (vacuum degree: 1 mmHg, and temperature: 28~33° C.), so as to obtain 3.64 kg of light-yellow oily 2-nitroethanol (80% yield, 98% purity (GC)).

Example 3

1.5 kg of Paraformaldehyde and 10 kg of nitromethane were added in a dry batch reactor, stirred, and then slowly added dropwise with 0.05 kg of a solution of potassium hydroxide in methanol. The reaction mixture was reacted under reflux for 0.5 h, cooled to room temperature, adjusted to pH 2~4 with concentrated hydrochloric acid, and concentrated under vacuum to recover nitromethane. Then the reaction mixture was added with 5 kg of amyl propionate at 0~5° C. for extraction, and the amyl propionate layer was collected, and dried under vacuum to recover the amyl propionate (vacuum degree: 2 mmHg, and temperature: 35~40° C.), so as to obtain 3.64 kg of light-yellow oily 2-nitroethanol (80% yield, 97% purity (GC)).

Example 4

1.5 kg of Paraformaldehyde and 10 kg of nitromethane were added in a dry batch reactor, stirred, and then slowly added dropwise with 0.05 kg of a solution of potassium hydroxide in methanol. The reaction mixture was reacted under reflux for 0.5 h, cooled down to room temperature, adjusted to pH 2~4 with acetic acid, and concentrated under vacuum to recover nitromethane. Then the reaction mixture was added with 6 kg of propyl valerate at 15~20° C. for extraction, and the propyl valerate layer was collected, and dried under vacuum to recover the propyl valerate (vacuum degree: 2 mmHg, and temperature: 37~41° C.), so as to obtain 3.64 kg of light-yellow oily 2-nitroethanol (80% yield, 98% purity (GC)).

Example 5

3 kg of Paraformaldehyde and 20 kg of nitromethane were added in a dry batch reactor, stirred, and then slowly added dropwise with 0.1 kg of a solution of potassium hydroxide in methanol. The reaction mixture was reacted under reflux for 0.5 h, cooled to room temperature, adjusted to pH 2~4 with acetic acid, and concentrated under vacuum to recover nitromethane. Then the reaction mixture was added with 12 kg of propyl valerate at 0~5° C., and subjected to extraction in continuous extraction equipment (CINC Deutschland GmbH & Co. KG), and the propyl valerate layer was collected, and dried under reduced pressure to recover the propyl valerate (vacuum degree: 1 mmHg, and temperature: 33~36° C.), so as to obtain 7.76 kg of light-yellow oily 2-nitroethanol (85% yield, 98% purity (GC)).

Example 6

3 kg of Paraformaldehyde and 20 kg of nitromethane were added in a dry batch reactor, stirred, and then slowly added dropwise with 0.1 kg of a solution of potassium hydroxide in methanol. The reaction mixture was reacted under reflux for 0.5 h, cooled to room temperature, adjusted to pH 2~4 with concentrated sulfuric acid, and concentrated under vacuum to recover nitromethane. Then the reaction mixture was added with 10 kg of amyl propionate at 20~25° C., and subjected to extraction in continuous extraction equipment, and the amyl propionate layer was collected, and dried under reduced pressure to recover the amyl propionate (vacuum degree: 1 mmHg, and temperature: 29~32° C.), so as to obtain 7.55 kg of light-yellow oily 2-nitroethanol (83% yield, 97% purity (GC)).

Example 7

3 kg of Paraformaldehyde and 20 kg of nitromethane were added in a dry batch reactor, stirred, and then slowly added dropwise with 0.1 kg of a solution of potassium hydroxide in methanol. The reaction mixture was reacted under reflux for 0.5 h, cooled to room temperature, adjusted to pH 2~4 with concentrated sulfuric acid, and concentrated under vacuum to recover nitromethane. Then the reaction mixture was added with 9 kg of isobutyl butyrate at 10~15° C., and subjected to extraction in continuous extraction equipment, and the isobutyl butyrate layer was collected, and dried under reduced pressure to recover the isobutyl butyrate (vacuum degree: 1 mmHg, and temperature: 28~32° C.), so as to obtain 7.55 kg of light-yellow oily 2-nitroethanol (83% yield, 98% purity (GC)).

Described above are merely illustrative of the technical solutions of the disclosure, which are not intended to limit the disclosure. It should be understood that any modifications and replacements made by those skilled in the art without departing from the spirit of the disclosure should fall within the scope of the disclosure defined by the appended claims.

What is claimed is:

1. A separation and purification method of 2-nitroethanol (I), comprising:

(a) reacting paraformaldehyde with nitromethane under the catalysis of a base to obtain a mixture of 2-nitroethanol (I), 2-nitro-1,3-propanediol (II) and tris(hydroxymethyl) nitromethane (III), as shown in the following reaction scheme:

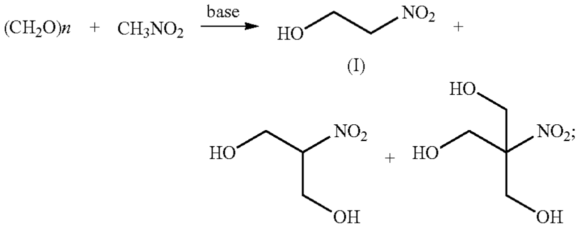

(I) (II) (III)

and (b) selecting an extraction solvent in which the 2-nitroethanol (I), 2-nitro-1,3-propanediol (II) and tris(hydroxymethyl) nitromethane (III) are different in solubility; adding the extraction solvent to the mixture followed by extraction, separation, and vacuum concentration to obtain the 2-nitroethanol (I);

wherein the extraction solvent is one or more of $C_3$~$C_9$ aliphatic esters;

a mass ratio of the extraction solvent to the paraformaldehyde is (1~10): 1;

the extraction is performed at −20~60° C. in a kettle equipment or a continuous extraction equipment; and the vacuum concentration is performed under a vacuum degree of 0.1~10 mmHg at 0~60° C.

2. The separation and purification method of claim 1, wherein the extraction solvent is selected from the group consisting of butyl propionate, amyl propionate, propyl butyrate, butyl butyrate, isobutyl butyrate, tert-butyl butyrate, amyl butyrate, propyl isobutyrate, butyl isobutyrate, propyl valerate, isopropyl valerate, butyl valerate, isobutyl valerate, tert-butyl valerate, ethyl cyclopentanecarboxylate, propyl cyclopentanecarboxylate, and a mixture thereof.

3. The separation and purification method of claim 1, wherein the mass ratio of the extraction solvent to the paraformaldehyde is (1~5): 1.

4. The separation and purification method of claim 1, wherein the extraction is performed at −20~30° C.

5. The separation and purification method of claim 1, wherein the continuous extraction equipment is a continuous membrane extraction-membrane separation equipment, a continuous micromixer mixing-microchannel reactor extraction-gravity sedimentation separation equipment, and a continuous centrifugal mixing-centrifugal separation equipment.

6. The separation and purification method of claim 1, wherein the vacuum concentration is performed under a vacuum degree of 0.1~5 mmHg at 0~40° C.

* * * * *